(12) United States Patent
Graham

(10) Patent No.: US 8,162,869 B2
(45) Date of Patent: Apr. 24, 2012

(54) HYBRID COMPRESSION GARMET

(75) Inventor: Joseph A. Graham, Canton, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 390 days.

(21) Appl. No.: 12/500,729

(22) Filed: Jul. 10, 2009

(65) Prior Publication Data
US 2011/0009795 A1  Jan. 13, 2011

(51) Int. Cl.
A61H 7/00 (2006.01)
A61L 15/00 (2006.01)
A61F 5/37 (2006.01)
A61F 13/06 (2006.01)

(52) U.S. Cl. .......... 602/62; 601/133; 601/134; 601/148; 601/151; 602/75; 128/882

(58) Field of Classification Search .............. 601/41–44, 601/61, 71, 133–134, 143–144, 147, 33–34, 601/148–151; 606/201, 203; 602/60–66, 602/75; 128/876, 877–882, 869
See application file for complete search history.

(56) References Cited

U.S. PATENT DOCUMENTS

| | | | |
|---|---|---|---|
| 3,826,249 A | 7/1974 | Lee et al. | |
| 5,342,285 A | 8/1994 | Dye | |
| 5,403,265 A | 4/1995 | Berguer et al. | |
| 5,653,244 A | 8/1997 | Shaw | |
| 5,725,485 A | 3/1998 | Ribando et al. | |
| 5,795,312 A | 8/1998 | Dye | |
| 5,891,065 A | 4/1999 | Cariapa et al. | |
| 5,918,602 A | 7/1999 | Shaw et al. | |
| 6,007,559 A * | 12/1999 | Arkans | 606/201 |
| 6,109,267 A * | 8/2000 | Shaw et al. | 128/882 |
| 6,338,723 B1 | 1/2002 | Carpenter et al. | |
| 6,375,633 B1 | 4/2002 | Endress et al. | |
| 6,589,194 B1 | 7/2003 | Calderon et al. | |
| 7,270,642 B2 | 9/2007 | Ouchene et al. | |
| 7,329,232 B2 | 2/2008 | Lipshaw et al. | |
| 7,618,384 B2 * | 11/2009 | Nardi et al. | 601/149 |
| 2005/0043657 A1 * | 2/2005 | Couvillon, Jr. | 601/134 |
| 2005/0187503 A1 | 8/2005 | Tordella et al. | |
| 2005/0222526 A1 | 10/2005 | Perry et al. | |
| 2006/0287621 A1 | 12/2006 | Atkinson et al. | |
| 2007/0049853 A1 | 3/2007 | Adams et al. | |
| 2007/0055188 A1 | 3/2007 | Avni et al. | |
| 2007/0173886 A1 | 7/2007 | Rousso et al. | |

* cited by examiner

*Primary Examiner* — Patricia Bianco
*Assistant Examiner* — George N Phillips
(74) *Attorney, Agent, or Firm* — Thomas M. Johnston, Esq.

(57) ABSTRACT

A hybrid compression garment comprises a sleeve adapted for placement on a limb of a person for applying static compression to the limb. A connecting device on the sleeve enables releasable connection of the sleeve to a machine. The machine is independent of the sleeve and operable to transmit, through the connecting device, a force to the sleeve that constricts the sleeve without inflating the sleeve to apply active compression to the limb. The connecting device is adapted for connection of the sleeve to the machine such that the sleeve can be used to apply active compression to the limb and adapted for disconnection of the sleeve from the machine such that the sleeve can be used to apply static compression to the limb. A method of applying compression to a limb of a person is also disclosed.

15 Claims, 16 Drawing Sheets

HYBRID COMPRESSION GARMET

FIELD OF THE INVENTION

The present invention generally relates to compression garments, and more particularly to a static compression sleeve configured for releasable connection to a machine for applying active compression.

BACKGROUND OF THE INVENTION

Compression garments for applying compressive forces to a selected area of a patient's anatomy are used in many situations. For example, compression garments may be used to treat venous insufficiency or edema, to heal wounds, or to prevent deep vein thrombosis (DVT). Some compression garments are used to apply static compression to a limb. Other compression garments are used to apply active compression to a limb. Active compression garments that provide intermittent pulses of compression in a sleeve are particularly useful. Cyclic application of pressure provides a non-invasive method of prophylaxis to reduce the incidence of DVT, and the like. These compression garments find particular use with high-risk patients suffering from, e.g., obesity, advanced age, malignancy, or prior thromboembolism. Such patients often have swelling (edema) and tissue breakdown (venous stasis ulcer) in the lower leg. If DVT occurs, the valves that are located within the veins of the leg can be damaged, which in turn can cause stasis and high pressure in the veins of the lower leg.

When these patients are ambulatory, static compression garments are often adequate to augment blood circulation or lymphatic flow. An example of a static compression garment is a compression stocking. Compression stockings apply static compression that assists in blood circulation and lymphatic flow when combined with the muscle pump effect of walking or other movement of the leg and/or foot. Compression stockings may be configured to apply graduated static compression such that a maximum compression is applied at the ankle and a minimum compression is applied at the thigh. Such graduated compression further promotes blood flow up the leg towards the heart.

When these patients are stationary, however, active compression is often required to provide sufficient enhancement of venous and lymphatic flow. Active compression garments are generally used to provide intermittent pulses of compression to a limb. Such garments are capable of providing sequential and gradient compression to further enhance venous and lymphatic flow. Many active compression garments are connected to a source of compressed air for inflating bladders on the garment. Patients apply the active compression garment to a respective limb before every active therapy session and remove the garment from the limb after completion of the therapy session. Repeated application and removal of active compression garments can be time consuming and inconvenient, especially for patients with limited dexterity. Such factors lead to decreased patient compliance and thus ineffective compression therapy.

SUMMARY OF THE INVENTION

It would be desirable to have a hybrid compression garment that combines the advantages of static and active compression garments. The garment could be worn by patients while they are ambulatory to provide static compression. When the patient is stationary, the garment could be interfaced with a machine to provide active compression. Such a garment would not require patients to apply a different compression garment before an active compression therapy session and remove the garment after the completion of the session. Thus, patient compliance and the effectiveness of compression therapy would be increased, among other benefits.

In one aspect, a hybrid compression garment generally comprises a sleeve adapted for placement on a limb of a person for applying static compression to the limb. The garment further comprises a connecting device on the sleeve for releasable connection of the sleeve to a machine that is independent of the sleeve and operable to transmit, through the connecting device, a force to the sleeve that constricts the sleeve without inflating the sleeve to apply active compression to the limb. The connecting device is adapted for connection of the sleeve to the machine such that the sleeve can be used to apply active compression to the limb and is adapted for disconnection of the sleeve from the machine such that the sleeve can be used to apply static compression to the limb.

In another aspect, a method of applying compression to a limb of a person generally comprises placing a sleeve on the limb for applying static compression to the limb and interfacing a connecting device on the sleeve with a machine that is independent of the sleeve. The method further comprises constricting the sleeve without inflating the sleeve by transmitting a force generated by the machine to the sleeve through the connecting device for applying active compression to the limb.

Other objects and features will be in part apparent and in part pointed out hereinafter.

DETAILED DESCRIPTION

Figure 1:
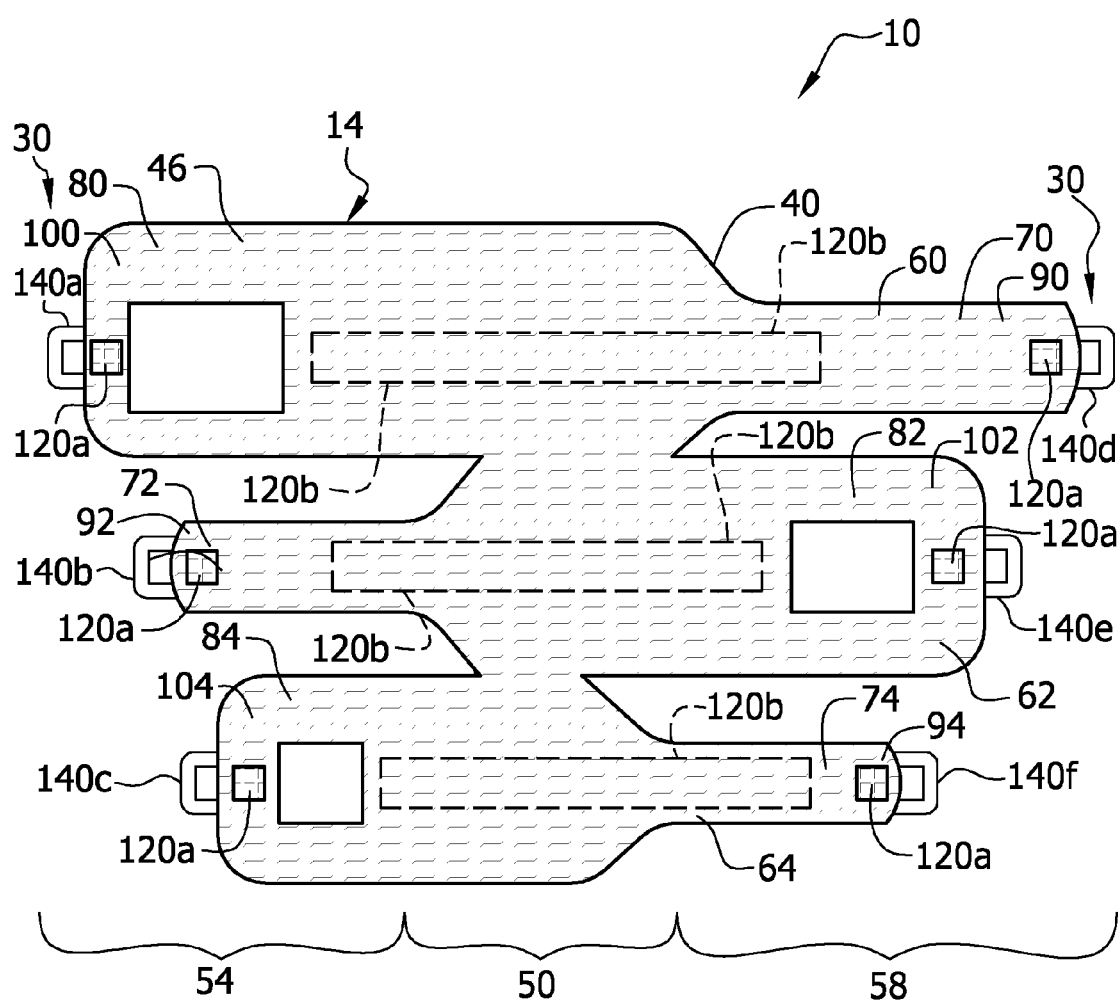
FIG. 1 is a front elevation of a first embodiment of a hybrid compression garment of this invention.
Figure 2:
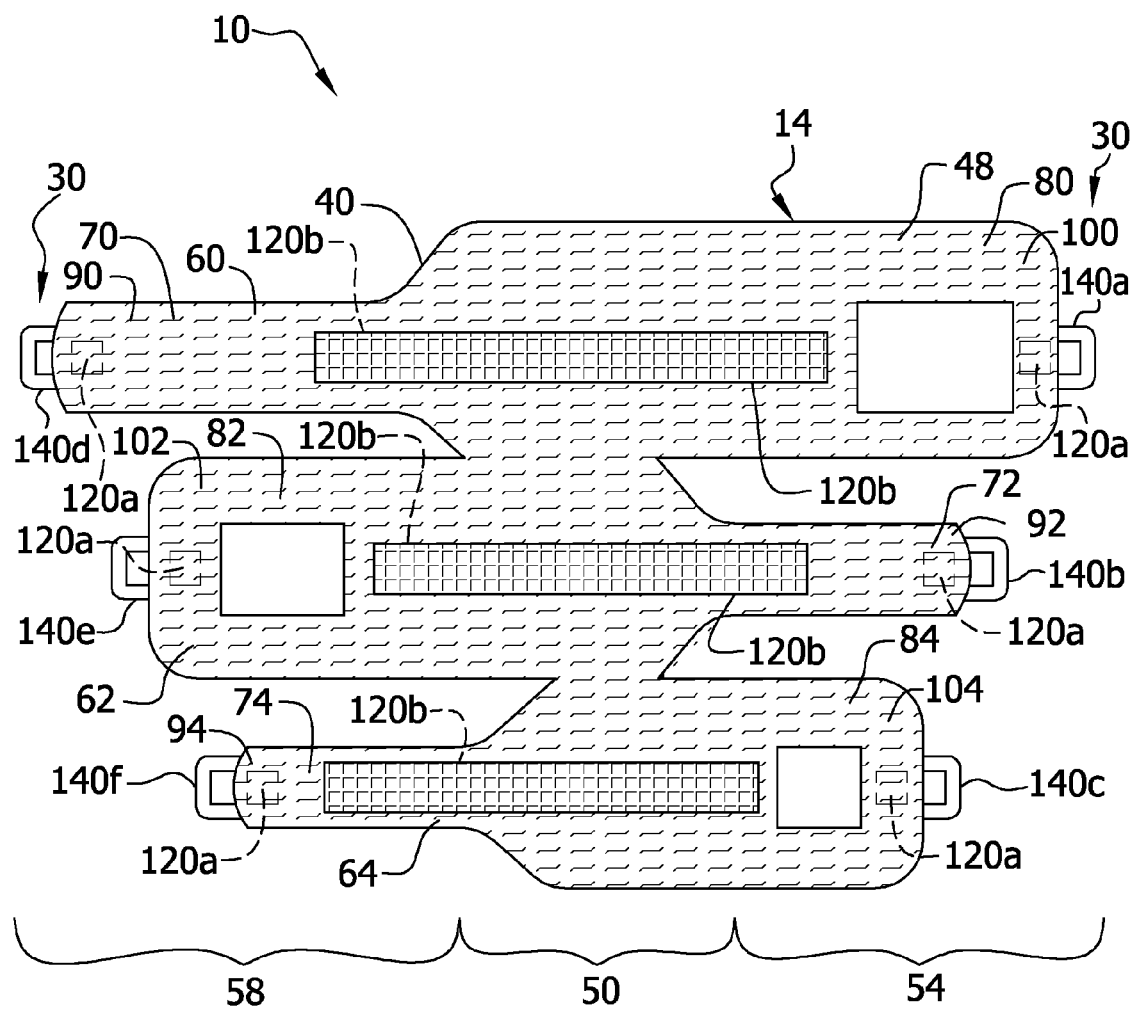
FIG. 2 is a back elevation of the garment of FIG. 1.

Referring to the drawings, FIGS. 1 and 2 show a hybrid compression garment, generally designated 10. The garment 10 comprises a sleeve 14 that may be used to apply static and active compression to a limb L of a person. The sleeve 14 may be worn by a person while ambulatory or stationary for applying static compression. While the person is stationary, the sleeve 14 may be used to apply active compression to the limb L by connecting the sleeve 14 to a machine 20. As described in further detail below, the machine 20 is independent of the sleeve 14 and operable to transmit a force to the sleeve that constricts the sleeve without inflating the sleeve to apply active compression to the limb L. A connecting device 30 on the sleeve 14 is adapted for releasable connection of the sleeve to the machine 20 such that the sleeve can be used to apply active compression to the limb L. The connecting device 30 is also adapted for disconnection of the sleeve 14 from the machine 20 such that the sleeve can be used to apply static compression to the limb L. Thus, both static and active compression may be applied using the same sleeve 14.

Figure 3A:
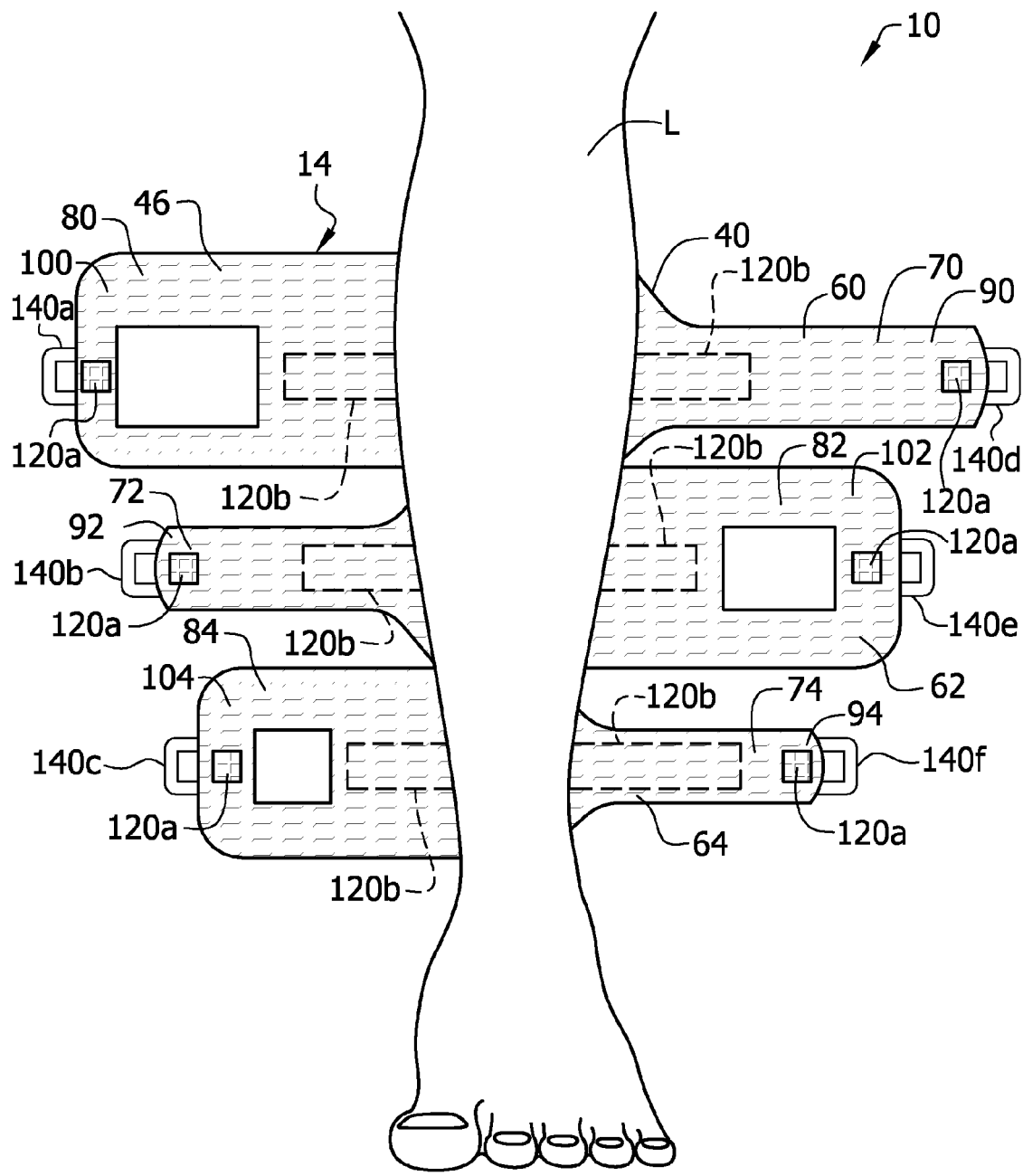
FIG. 3A is a front elevation of the garment showing a leg placed over the garment.
Figure 3B:
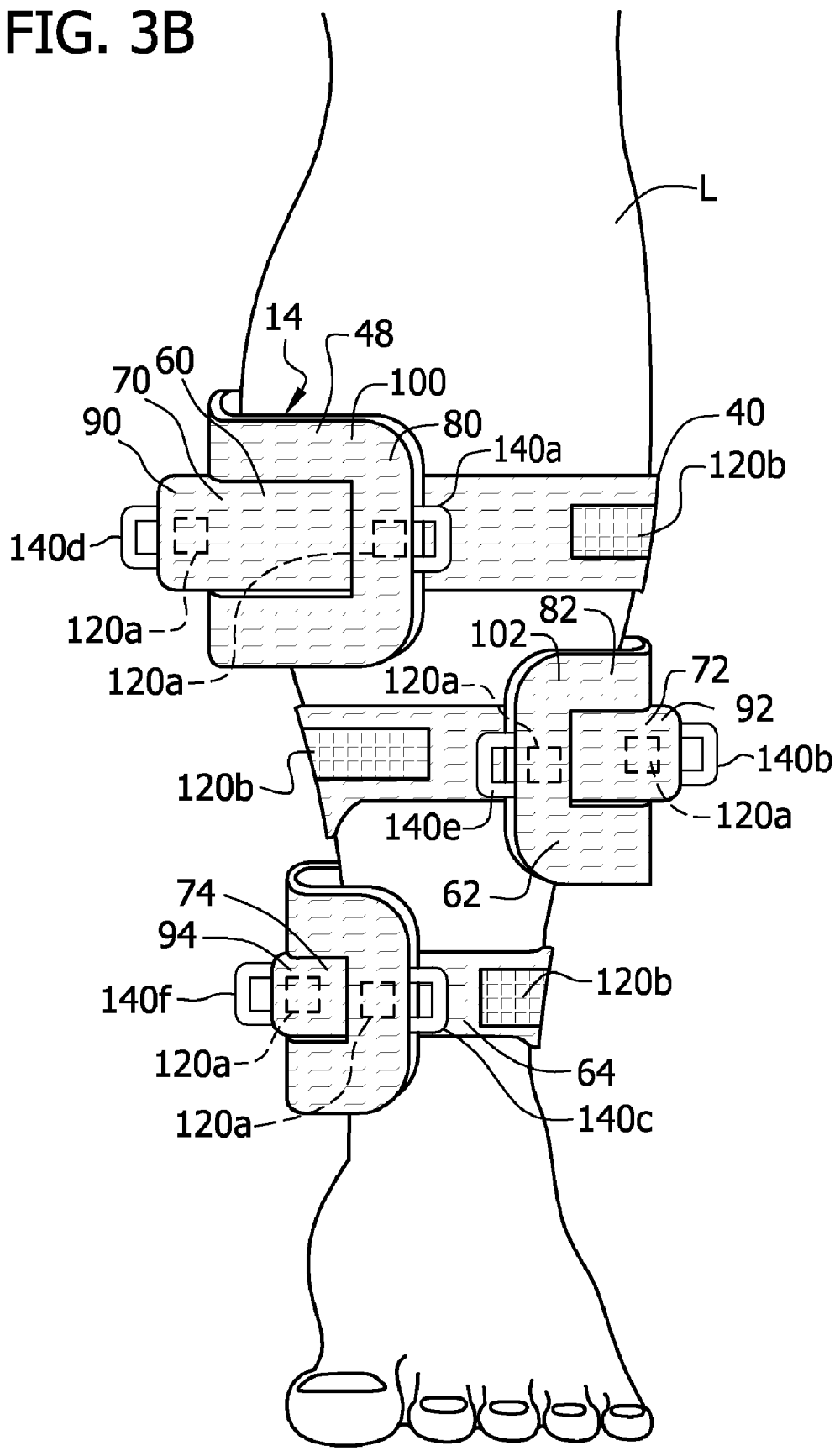
FIG. 3B is a view similar to FIG. 3A but showing the garment partially wrapped on the leg.

The sleeve 14 comprises a sleeve body 40 made of flexible fabric. The sleeve body 40 comprises an inside or patient contact surface 46 (FIG. 1) and an outside surface 48 (FIG. 2) that faces outward when the sleeve is placed on a limb L. The fabric may be inelastic or elastic, and the fabric may be porous to allow for breathability. The sleeve body 40 comprises a longitudinal central portion, generally designated 50, and left and right side portions, generally designated 54 and 58. The left and right side portions 54, 58 are desirably formed integrally with the central portion 50 and extend laterally outward from opposite sides of the central portion. The side portions 54, 58 are configured to overlap one another when the sleeve 14 is placed on the limb L. More specifically, as shown in sequence in FIGS. 3A-3C, the sleeve body 40 is configured such that when the central portion 50 is longitudinally aligned with a person's limb L, the side portions 54, 58 may be folded over the limb and overlapped such that the sleeve 14 encircles the limb. The sleeve body 40 may have different general configurations. For example, the sleeve body 40 may have a continuous tube or other configuration in which the sleeve 14 is placed on a limb L by sliding it over the limb, like a sock.

In the illustrated embodiment, the side portions 54, 58 comprise a plurality of sets 60, 62, 64 of straps 70, 72, 74 and loops 80, 82, 84. Three sets 60, 62, 64 are shown, but any suitable number may be used. Each set 60, 62, 64 comprises a respective strap 70, 72, 74 extending out from a longitudinal side of the central portion 50 and terminating in a free end 90, 92, 94 and a respective loop 80, 82, 84 extending out from an opposite side of the central portion and terminating in a free end 100, 102, 104. The strap 70, 72, 74 and loop 80, 82, 84 of a respective set 60, 62, 64 are generally in alignment with one another on opposite sides of the central portion 50. Thus, as shown in sequence in FIGS. 3A-3C, when the sleeve 14 is placed over the limb L, with the central portion 50 of the sleeve longitudinally aligned with the limb, the side portions 54, 58 of the sleeve may be folded over the limb and the free ends of the straps 90, 92, 94 threaded through corresponding loops 80, 82, 84. Other configurations of the side portions 54, 58 may be used.

In the illustrated embodiment, the strap and loop sets 60, 62, 64 have alternate orientations along the length of the sleeve 14. As shown in FIG. 1, for example, the first set 60, at the upper end of the sleeve 14, comprises the strap 70 and the loop 80. The strap 70 extends out from the right longitudinal side of the central portion 50, and the loop 80 extends out from the left side of the central portion. The second set 62 comprises the loop 82 extending out from the right longitudinal side of the central portion 50, and the strap 92 extending out from the left longitudinal side of the central portion. The third set 64, at the lower end of the sleeve 14, comprises the loop 84 and the strap 74, which extend in the same respective directions as the loop 80 and the strap 70 of the first set 60. Other suitable configurations may be used.

Fasteners 120a, 120b on the sleeve 14 are provided for holding the side portions 54, 58 in a position in which the sleeve encircles the limb L to apply static compression to the limb. The fasteners of the illustrated embodiment comprise hook fabric 120a and loop fabric 120b for holding the straps 70, 72, 74 and loops 80, 82, 84 in a position in which the sleeve 14 encircles the limb L. Small sections of hook fabric 120a are sewn or otherwise secured to the inside surface 46 of the sleeve 14 adjacent the strap free ends 90, 92, 94 and the loop free ends 100, 102, 104. Three elongate sections of loop fabric 120b are secured to the outside surface 48 of the sleeve 14, as shown in FIG. 2. The loop fabric 120b sections extend generally across the longitudinal central portion 50 of the sleeve body 40 and are aligned with respective strap and loop sets 60, 62, 64. These elongate sections of loop material 120b allow for an increased range of adjustment of the straps 70, 72, 74 and loops 80, 82, 84 to fit limbs of many sizes, as will become apparent. Alternatively, two or more sections of loop material 120b may be used for each strap and loop set 60, 62, 64. Other fasteners 120a, 120b may be used, such as clips, snaps, buckles, etc. The fasteners 120a, 120b may or may not need to be unfastened when the sleeve 14 is connected to the machine 20, as explained in further detail below.

Figure 3C:
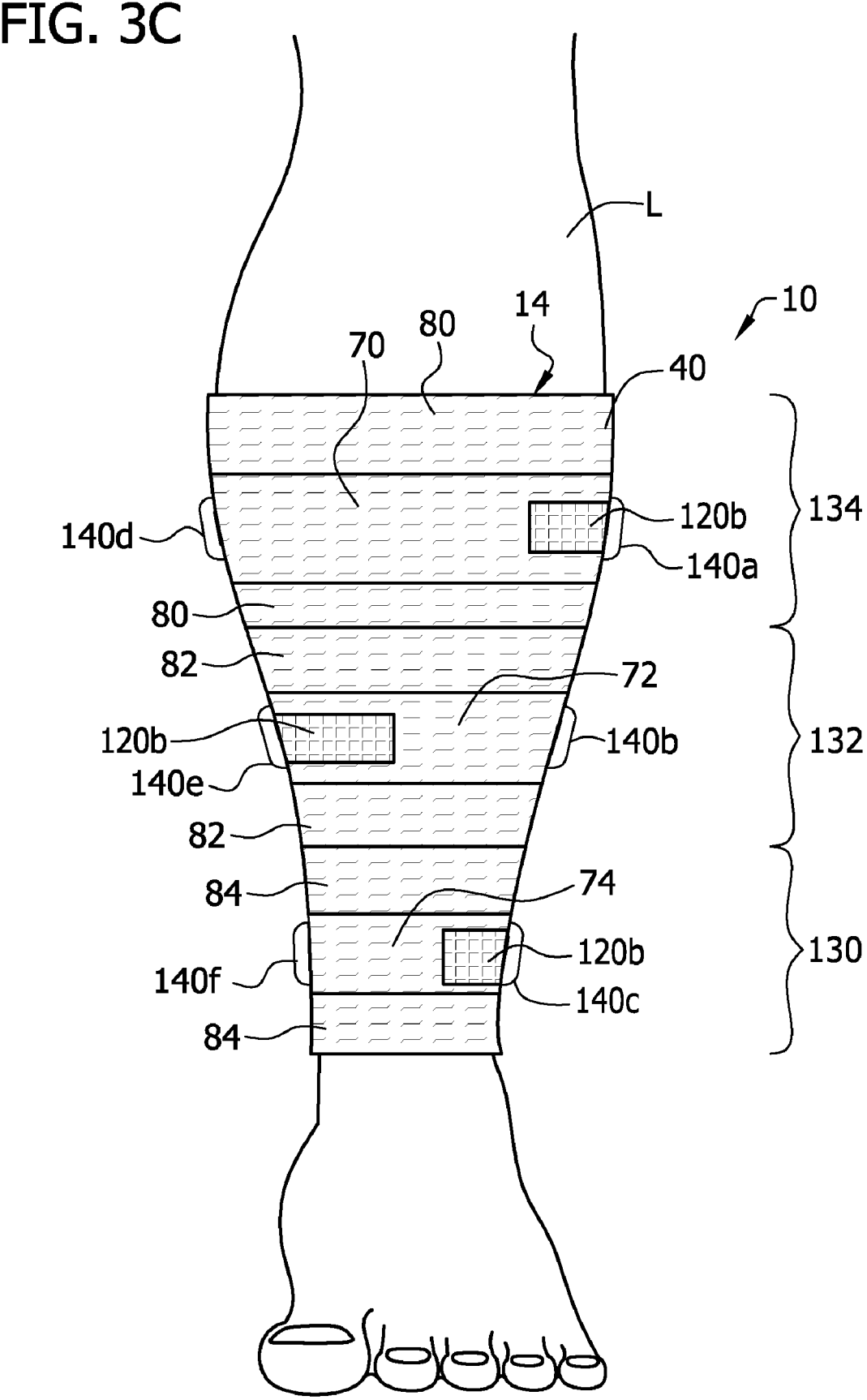
FIG. 3C is a view similar to FIG. 3B but showing the garment fully wrapped on the leg.
Figure 4:
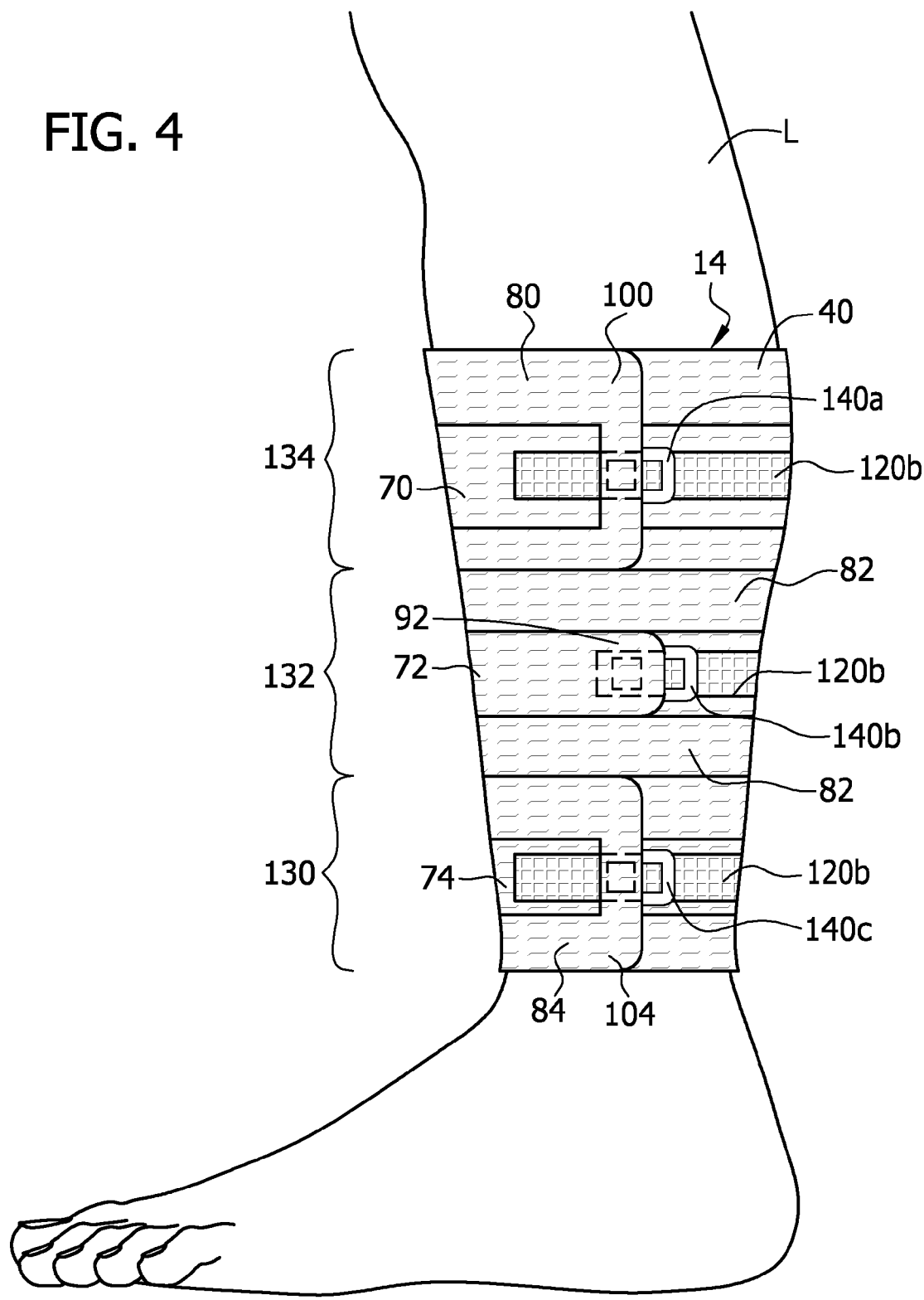
FIG. 4 is a right side elevation of the garment wrapped on the leg.

The compression garment 10 may be configured for use with an arm or a leg. In some embodiments, the garment has a length for encircling substantially all of an arm or leg. In other embodiments, the garment has a length for encircling only a portion of an arm or leg (e.g., a forearm). As discussed and illustrated herein, the garment is adapted for placement on a lower leg L. As shown in FIGS. 3c and 4, the garment 10 comprises three compression zones: an ankle compression zone 130; an intermediate compression zone 132; and a calf compression zone 134. The compression garment 10 may be configured to have more or fewer compression zones 130, 132, 134.

The connecting device 30 on the sleeve 14 is provided for releasable connection of the sleeve to the machine 20 for applying active compression. In the illustrated embodiment, the connecting device 30 comprises six connectors 140a-140f. The connectors 140a-140f are positioned and spaced along the length of the sleeve 14. Two of the connectors 140a-140f are mounted on the sleeve 14 within each compression zone 130, 132, 134. The connectors 140a-140f are desirably located on the sleeve 14 at locations such that when the sleeve is placed on a leg L the two connectors in each compression zone 130, 132, 134 are positioned on or adjacent opposite sides of the leg L. In the illustrated embodiment, the connectors 140a-140f are located on the opposite side portions 54, 58 of the sleeve body 40 such that the sleeve 14 constricts when forces are applied in opposite directions to the connectors on respective overlapping side portions of the sleeve. More specifically, as shown in sequence in FIGS. 3A-3C and 4, the connectors 140a-140f are mounted on or adjacent the free ends of the straps 90, 92, 94 and the free ends of the loops 100, 102, 104 such that when the side portions 54, 58 of the sleeve 14 are folded over the limb L and the free ends of the straps are threaded through corresponding loops 80, 82, 84 the connectors are generally on or adjacent the right and left sides of the leg.

The connectors 140a-140f may comprise hooks, loops, tabs, buckles, magnets, ties, snaps, or any other suitable connector. In the illustrated embodiment, the connectors 140a-140f are loops, also designated 140a-140f. The loops 140a-140f may be formed of a rigid material such as plastic or metal or be made of a flexible material such as a fabric or rope. The connectors 140a-140f may be mounted to the sleeve 14 by sewing, welding or any other suitable method. The connectors 140a-140f may be rigidly mounted to the sleeve 14 or may be mounted for rotational or swivel movement relative to the sleeve.

Figure 5:
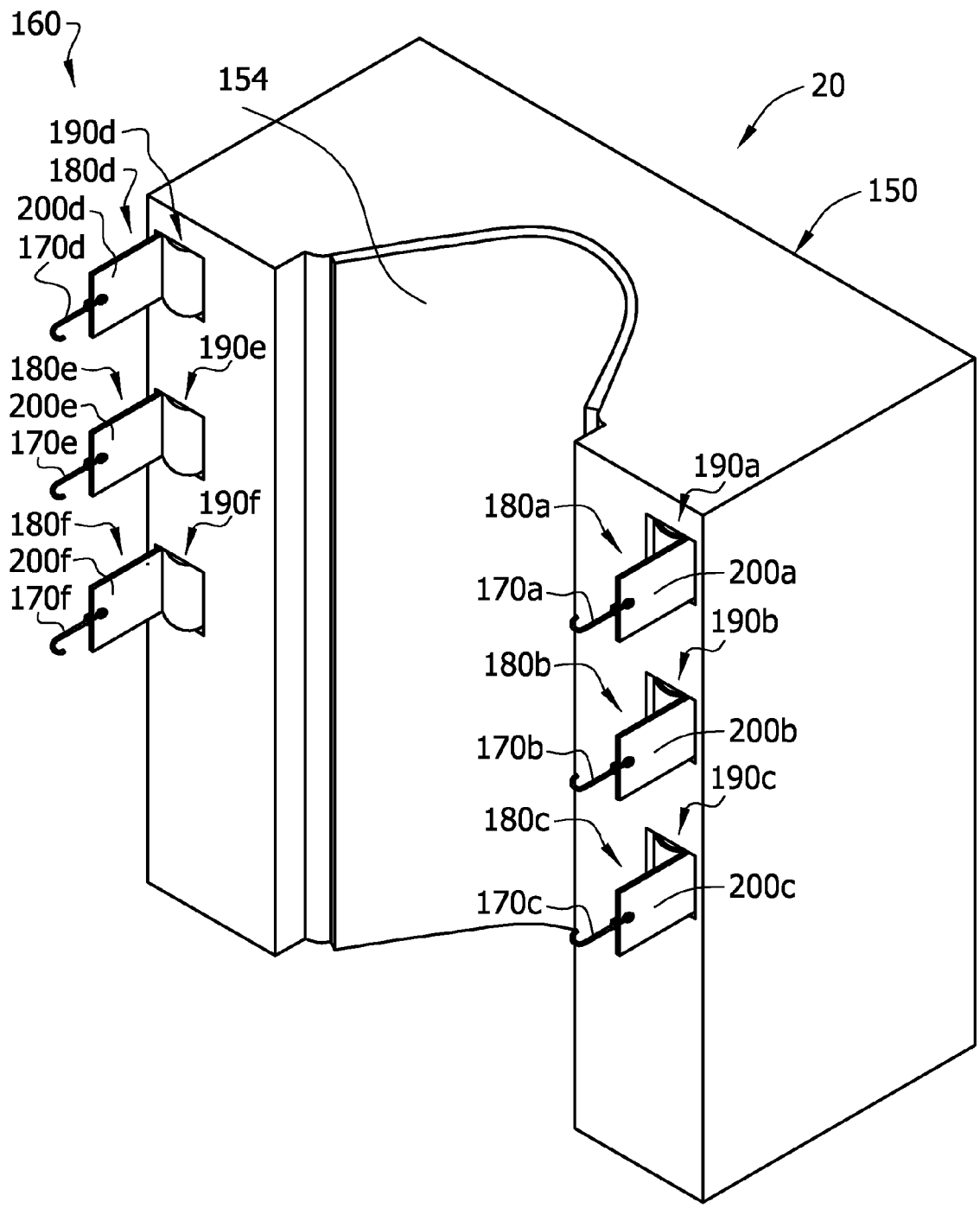
FIG. 5 is a perspective of a machine adapted for connection to the garment.

When a person wearing the sleeve 14 is stationary, the sleeve may be releasably connected to the machine 20 to apply active compression. As shown in FIG. 5, the machine 20 is independent of the sleeve 14. In other words, the machine 20 is separate from the sleeve 14 except for when the machine is connected to the sleeve to apply active compression. As explained above, the sleeve 14 is usable completely separate from the machine 20 to apply static compression to a limb L.

The machine 20 comprises a frame 150 and a bed 154 for supporting the limb L on which the sleeve 14 is wrapped. A person wearing the sleeve 14 may place their leg L on the bed 154 of the machine 20 while in a sitting or supine position. The frame 150 and bed 154 are shown as examples and may comprise any other suitable configurations.

The machine 20 further comprises an actuation system, generally designated 160, configured for releasable connection with the connecting device 30 on the sleeve 14. The machine 20 is operable to transmit, through the connecting device 30 of the sleeve 14, a force to the sleeve that constricts the sleeve without inflating the sleeve. More specifically, active compression is not achieved by inflating and deflating bladders on the sleeve 14. However, the sleeve 14 may have bladders (not shown). For example, the sleeve 14 may have one or more bladders that are inflated to and maintained at a certain inflation pressure to provide static compression to the limb L. Such bladders may remain inflated or be deflated before the sleeve 14 is connected to the machine 20 and the machine transmits, through the connecting device 30 of the sleeve 14, a force that constricts the sleeve without inflating the sleeve.

The actuation system 160 of the illustrated machine 20 comprises multiple connectors 170a-170f spaced along opposite sides of the bed 154 at intervals lengthwise of the bed generally corresponding to the spacing of the connectors 140a-140f along the sleeve 14. The illustrated connectors 170a-170f comprise hooks, also designated 170a-170f. The hooks 170a-170f are configured for releasable connection with the loops 140a-140f on the sleeve 14. Other types of connectors 170a-170f on the actuation system 160 or connectors 140a-140f on the sleeve 14 may be used to enable connection between the sleeve and machine 20.

Figure 6:
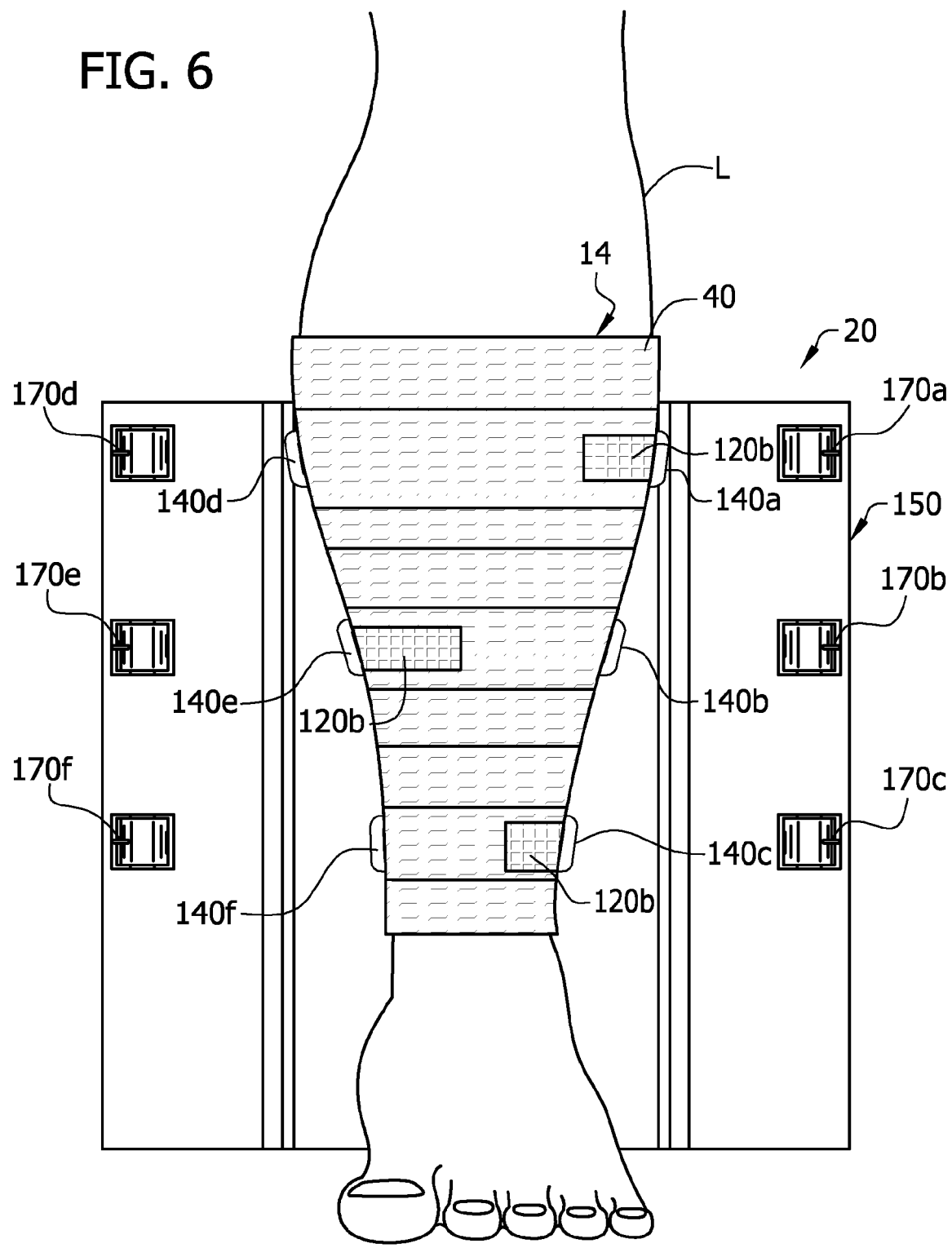
FIG. 6 is a front elevation of the machine of FIG. 5 showing the garment on the leg and the leg seated in the machine.
Figure 7:
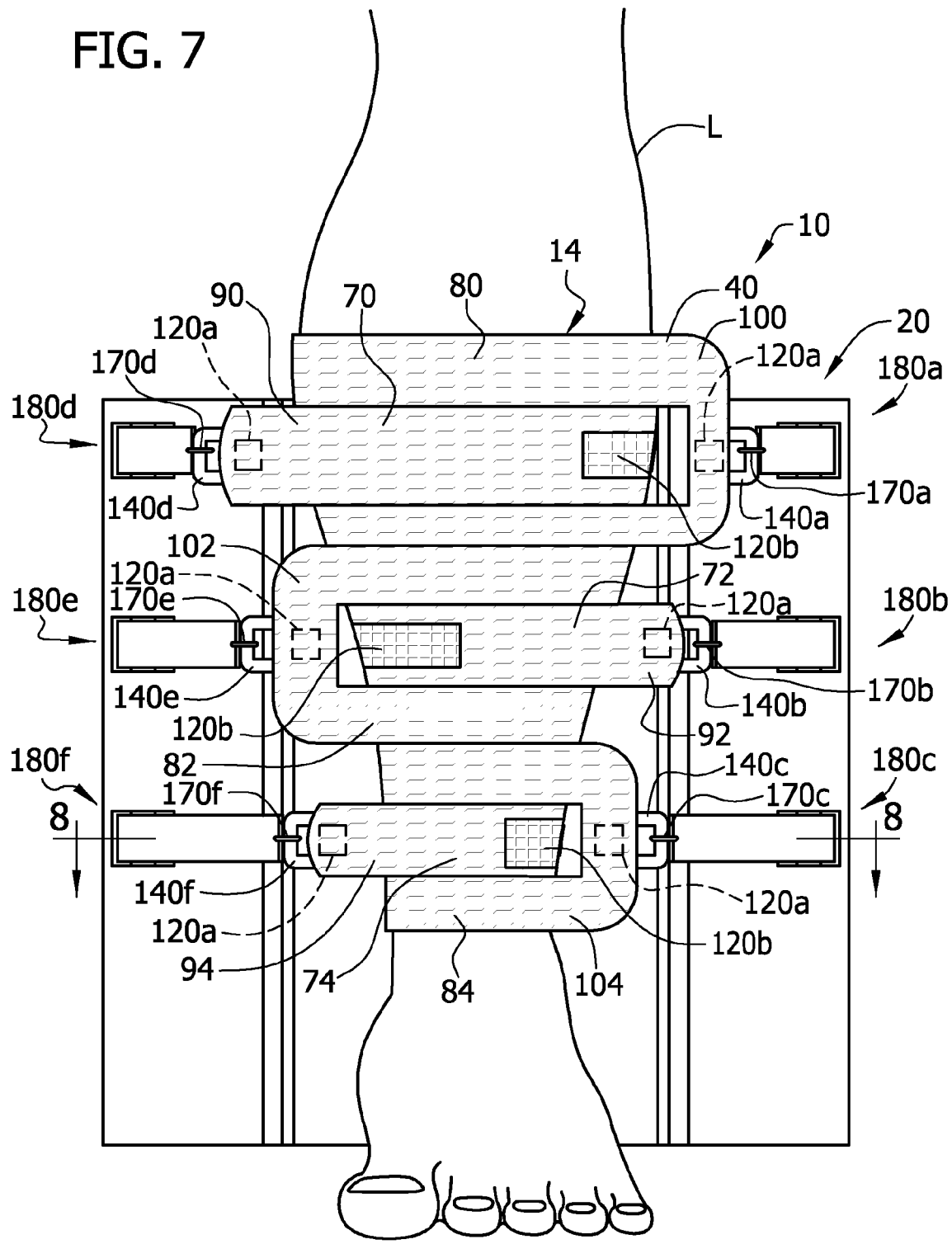
FIG. 7 is a view similar to FIG. 6 but showing connectors on the machine connected to connectors on the garment.

As shown by comparison of FIGS. 6 and 7, the free ends of the straps 90, 92, 94 and the free ends of the loops 100, 102, 104 may need to be unfastened from the sleeve 14 to enable connection of the hooks 170a-170f and loops 140a-140f. That is, unfastening the fasteners 120a, 120b may be necessary to place the side portions 54, 58 of the sleeve 14 in proper position for constriction of the sleeve by the machine 20. This unfastening may be necessary to prevent the fasteners 120a, 120b from impeding constriction of the sleeve 14, as described in further detail below.

Referring again to FIG. 5, the connectors 170a-170f on the machine 20 are mounted on one or more actuators 180a-180f on the machine frame 150. The actuators 180a-180f may comprise one or more solenoids or electric motors. Alternatively, a pneumatic system may be used to generate force for constricting the sleeve 14 without inflating the sleeve. Any other type of suitable actuators 180a-180f may be used. Each connector 170a-170f is desirably mounted on a separate actuator 180a-180f. Alternatively, one or more connectors 170a-170f may be mounted on a single actuator 180a-180f. For example, all of the connectors (e.g., 170a-170c) on one side of the bed 154 may be mounted or otherwise connected to a common actuator (e.g., one of 180a-180c).

The actuators 180a-180f are operable to transmit, through the connecting device 30 of the sleeve 14, a force to the sleeve that constricts the sleeve without inflating the sleeve to apply active compression to the limb L. The actuators 180a-180f move the connectors 170a-170f of the actuation system 160 such that when the connectors of the actuation system are connected to the connectors 140a-140f on the sleeve 14, forces in opposite directions are applied to respective overlapping side portions 54, 58 of the sleeve to constrict the sleeve. One or more actuators 180a-180f on at least one side of the bed 154 are moved to apply forces in opposite directions to respective overlapping side portions 54, 58 of the sleeve 14. Some of the connectors (e.g., 170a) on the machine 20 may be fixedly mounted on the machine, instead of mounted on an actuator (e.g., 180a), in which case the fixedly mounted connectors would remain stationary and a connector (e.g., 180d) on the opposite side of the bed 154 would be mounted on an actuator (e.g., 180d) for moving a respective sleeve connector (e.g., 140d) to constrict the sleeve 14.

In the illustrated embodiment, the machine 20 has six actuators 180a-180f, one for each hook 170a-170f. The actuators 180a-180f comprise spools 190a-190f driven by one or more electric motors, which are hidden from view within the machine. Belts 200a-200f are wrapped around respective spools 190a-190f, and the connector hooks 170a-170f are mounted on free ends of respective belts. To connect the hooks 170a-170f to the loops 140a-140f on the sleeve 14, the belts 200a-200f are partially unwound from the spools 190a-190f. The spools 190a-190f are rotatable in one direction tending to wind the belts 200a-200f onto the spools to constrict the sleeve 14 and rotatable in an opposite direction tending to unwind the belts to release the constriction on the sleeve. For example, as shown in FIG. 7, spool 190a is rotatable to the right to constrict the sleeve 14 and rotatable to the left to release constriction on the sleeve.

Figure 8:
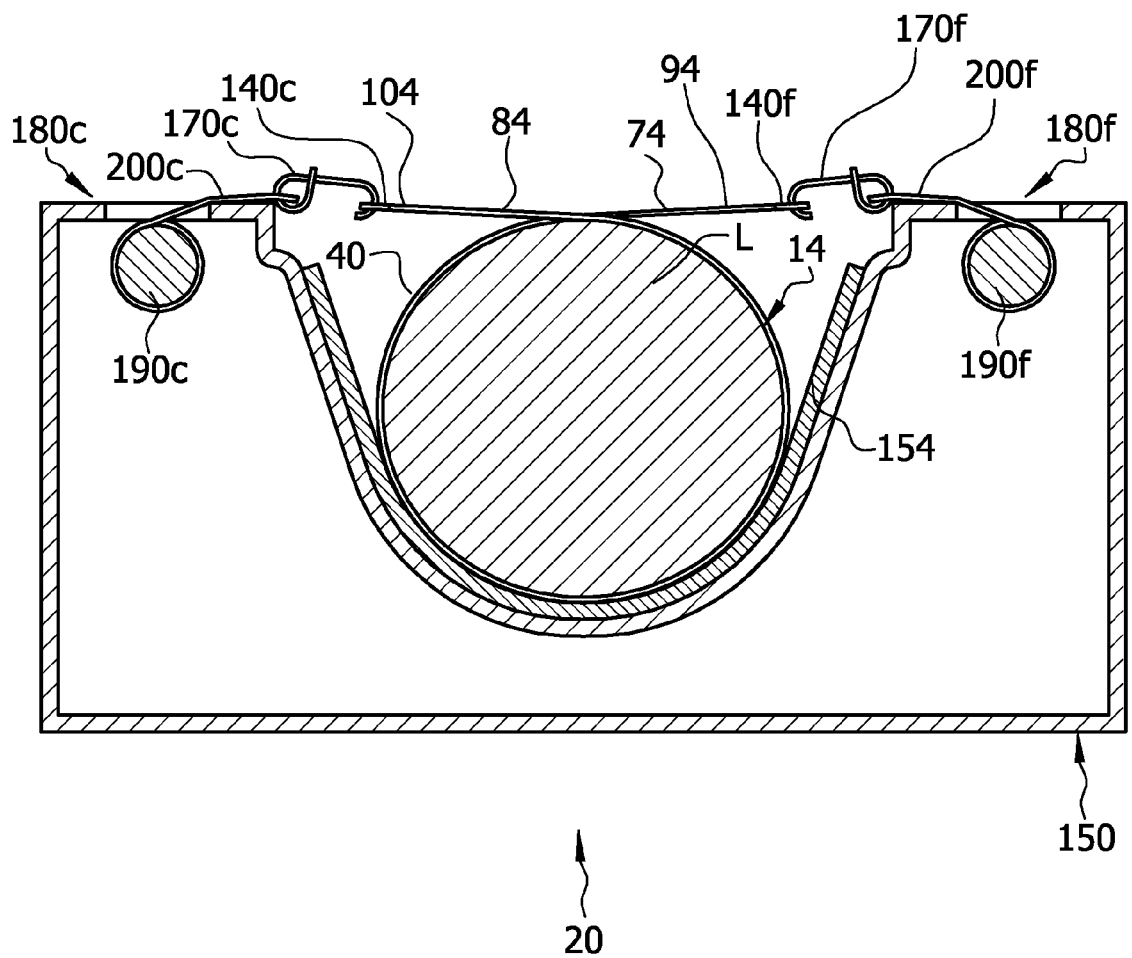
FIG. 8 is a section taken along the line 8-8 of FIG. 7.
Figure 9:
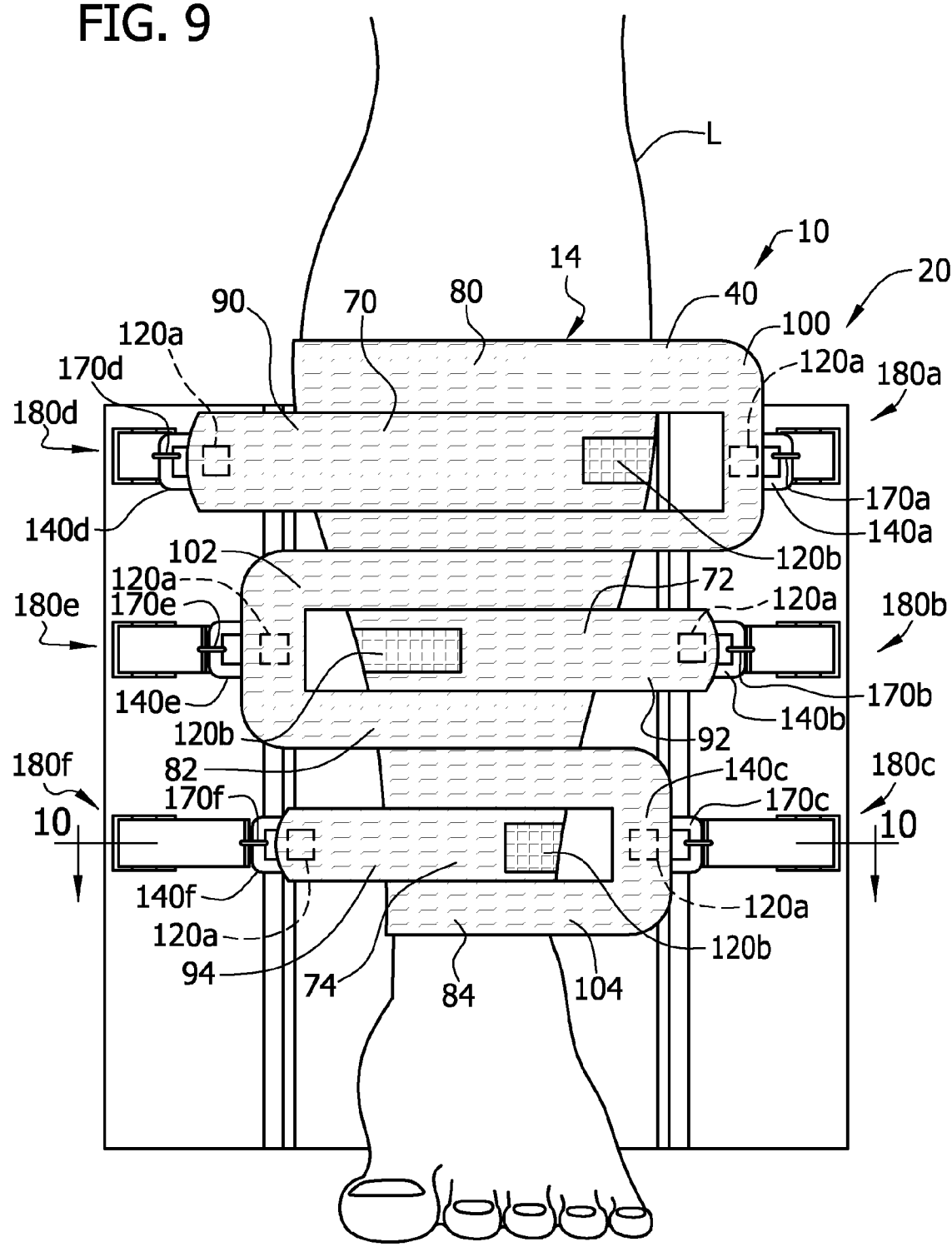
FIG. 9 is a view similar to FIG. 7 but showing the machine constricting the sleeve to apply compression to the leg.
Figure 10:
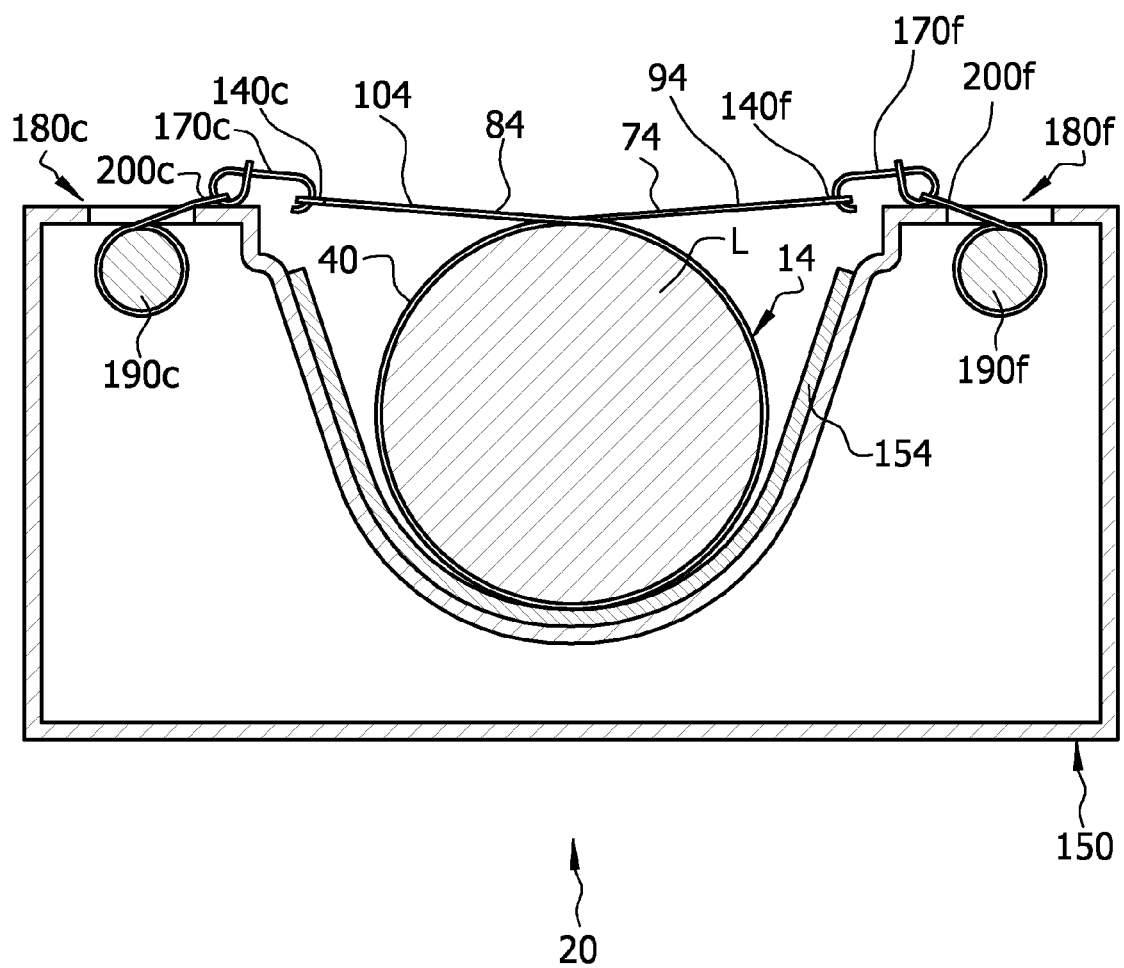
FIG. 10 is a section taken along the line 10-10 of FIG. 9.

As shown in FIG. 8, the actuators 180a-180f apply opposite forces to the free ends of the straps 90, 92, 94 and the free ends of the loops 100, 102, 104 to constrict the sleeve 14. Thus, the machine 20 is capable of constricting different compression zones 130, 132, 134 of the sleeve 14 at different times and at different magnitudes. This configuration enables the machine 20 to constrict distal portions of the sleeve 14 prior to constricting proximal portions of the sleeve to apply sequential compression to the limb L. For example, the ankle compression zone 130 may be constricted first, followed by the intermediate zone 132, and finally the calf zone 134. In addition, this configuration enables the machine 20 to constrict distal portions of the sleeve 14 more than proximal portions of the sleeve to apply gradient compression to the limb L. For example, the ankle compression zone 130 may be constricted more than the intermediate compression zone 132, and the intermediate compression zone more than the calf compression zone 134.

A controller (not shown), either integral with or independent of the machine 20, may be programmed to control the actuation system 160 and thus the constriction of the sleeve 14. Various regimens or parameters of active compression therapies including time, sequence, and/or gradient may be pre-programmed into the controller. The controller may also be manually programmed by a user. In some embodiments, the controller actively monitors the force applied to the sleeve 14 in one or more compression zones 130, 132, 134 and automatically adjusts to obtain optimal compression in each compression zone.

In use, the sleeve 14 is placed on the limb L by placing the central portion 50 of the sleeve in longitudinal alignment with the limb, with the inner or patient contact surface 46 of the sleeve facing the limb. The side portions 54, 58 of the sleeve 14 are then folded over the limb L and secured using the fasteners 120a, 120b such that the sleeve 14 encircles the limb to apply static compression to the limb. The side portions 54, 58 of the illustrated embodiment are folded over the limb L, and the free ends of the straps 90, 92, 94 are threaded through corresponding loops 80, 82, 84 before securing the free ends of the straps and loops using the hook and loop fabric sections 120a, 120b. This configuration enables the sleeve 14 to be adjusted to fit various sized limbs L. In addition, the sleeve 14 may be adjusted to apply static compression in different magnitudes in different compression zones 130, 132, 134. For example, the static compression applied in the ankle compression zone 130 may be greater than the compression applied in the intermediate compression zone 132, and the compression applied in the intermediate compression zone may be greater than the compression applied in the calf compression zone 134. The sleeve 14 thus may be worn by a person while ambulatory or stationary to provide uniform or gradient static compression to a limb L.

When the person wearing the sleeve 14 is stationary, the connecting device 30 on the sleeve may be interfaced with the actuation system 160 of the machine 20. While in a sitting or supine position, the person places the limb L on which the sleeve 14 is worn onto the bed 154 of the machine, as shown in FIG. 6. The multiple connectors 140a-140f on the sleeve 14 are then releasably connected with respective connectors 170a-170f of the actuation system 160 on the machine 20. As shown in FIG. 7, the hooks 170a-170f of the actuation system 160 are connected to the loops 140a-140f on the sleeve 14. The fasteners 120a, 120b on the sleeve 14 may need to be unfastened to connect the hooks 170a-170f of the actuation system 160 to the loops 140a-140f on the sleeve.

The sleeve 14 is then constricted by transmitting a force from the machine 20 to the sleeve through the connecting device 30 for applying active compression to the limb L. The sleeve 14 is not constricted by inflating the sleeve. Instead, the machine 20 applies forces to respective overlapping side portions 54, 58 of the sleeve 14 in opposite directions to constrict the sleeve, as is shown by comparison of FIGS. 7 and 9 and FIGS. 8 and 10. The sleeve 14 may be constricted intermittently to apply active compression. Thus, one or more compression zones 130, 132, 134 of the sleeve 14 may be constricted for a first length of time, relaxed for a second length of time, constricted again, and so forth. Distal portions of the sleeve 14 (e.g., ankle compression zone 130) may be constricted prior to constricting proximal portions (e.g., calf compression zone 134) of the sleeve to apply sequential compression to the limb L. Further, distal portions of the sleeve 14 may be constricted more than proximal portions of the sleeve to apply gradient compression to the limb L. A controller may be used to control the constriction of the sleeve 14 according to pre-installed programs or user input. Further, the controller may actively monitor the force applied to the sleeve 14 in one or more compression zones 130, 132, 134 and automatically adjust to achieve optimal compression in each compression zone.

Active compression may be terminated by discontinuing constriction of the sleeve 14 and disconnecting the sleeve from the machine 20. The person wearing the sleeve 14 may continue wearing the sleeve to apply static compression while the person is thereafter stationary or ambulatory. The fasteners 120a, 120b on the sleeve 14 may need to be adjusted or refastened for holding the side portions 54, 58 in a position in which the sleeve encircles the limb L to apply the desired static compression to the limb.

FIGS. 11-14 show a second embodiment of a hybrid compression garment 10'. The garment 10' is similar in some respects to the garment 10 described above, and corresponding parts are designated by the corresponding reference numbers, plus a prime designator ('). In this embodiment, the sleeve 14' comprises at least one constriction member 220a-220c that resides inside the sleeve body 40'. The machine 20' is connected to the constriction member 220a-220c and transmits a force to the constriction member to constrict the sleeve 14'.

Figure 11:
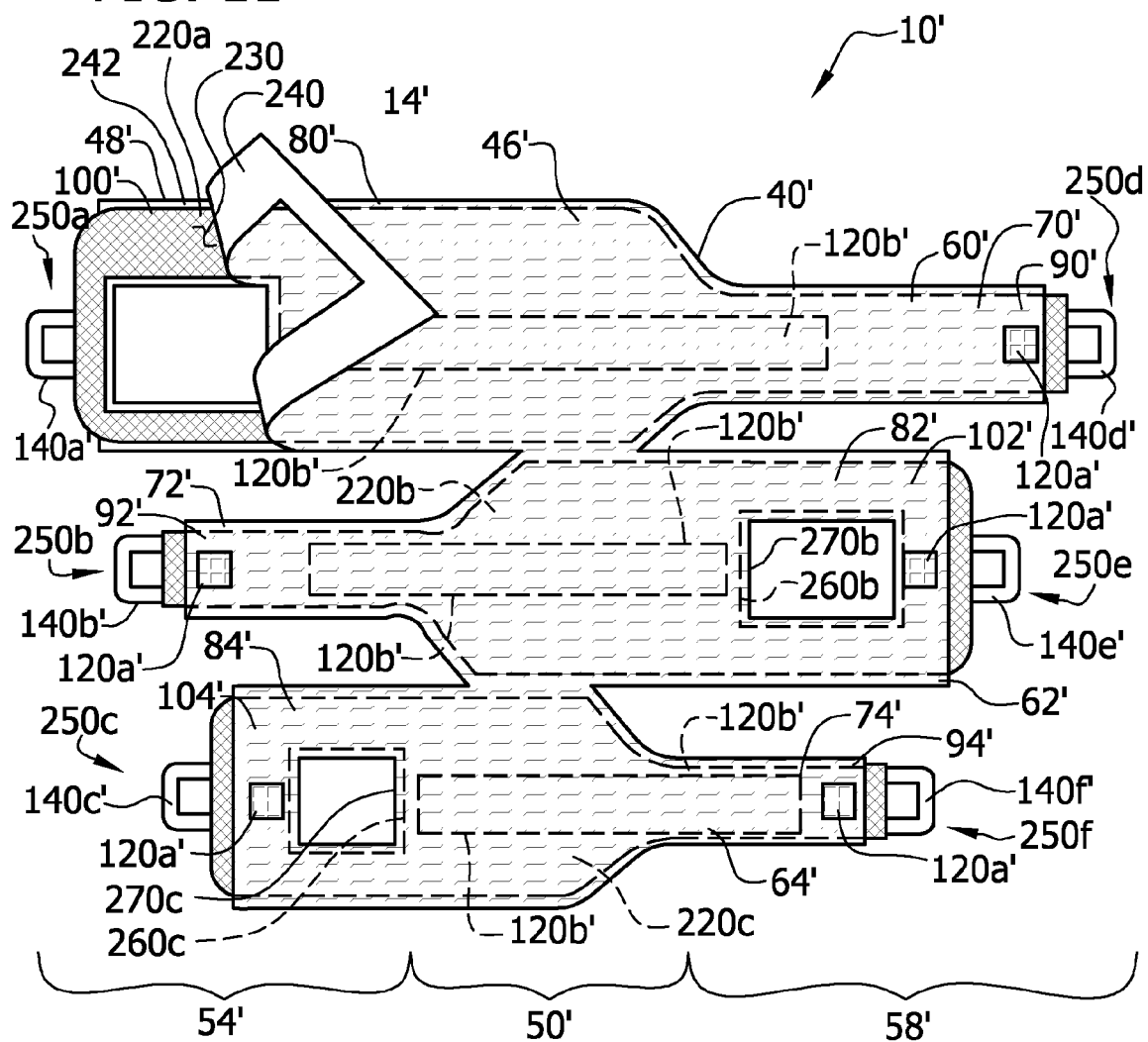
FIG. 11 is a front elevation of a second embodiment of a hybrid compression garment, the garment having constriction members shown in broken lines, a portion of the garment being pulled away to reveal part of one of the constriction members.

As shown in FIG. 11, the sleeve 14' of the illustrated embodiment comprises three separate constriction members 220a-220c. One constriction member 220a-220c is provided for each strap and loop set 60', 62', 64'. The constriction members 220a-220c are disposed in one or more cavities 230 of the sleeve body 40' between the patient contact (inside) surface 46' and the outside surface 48' of the sleeve body such that the constriction members are at least partially encapsulated by the sleeve body. A separate cavity 230 may be provided for each constriction member 220a-220c. In the illustrated embodiment, the sleeve body 40' has a single cavity 230 having a shape approximating the outline of the sleeve body. The cavity 230 may be formed, for example, by sewing or otherwise securing an edge margin of a patient contact layer 240 comprising the inside (patient contact) surface 46' of the sleeve body 40' to an edge margin of an outside layer 242 comprising the outside surface 48' of the sleeve body.

Figure 12:
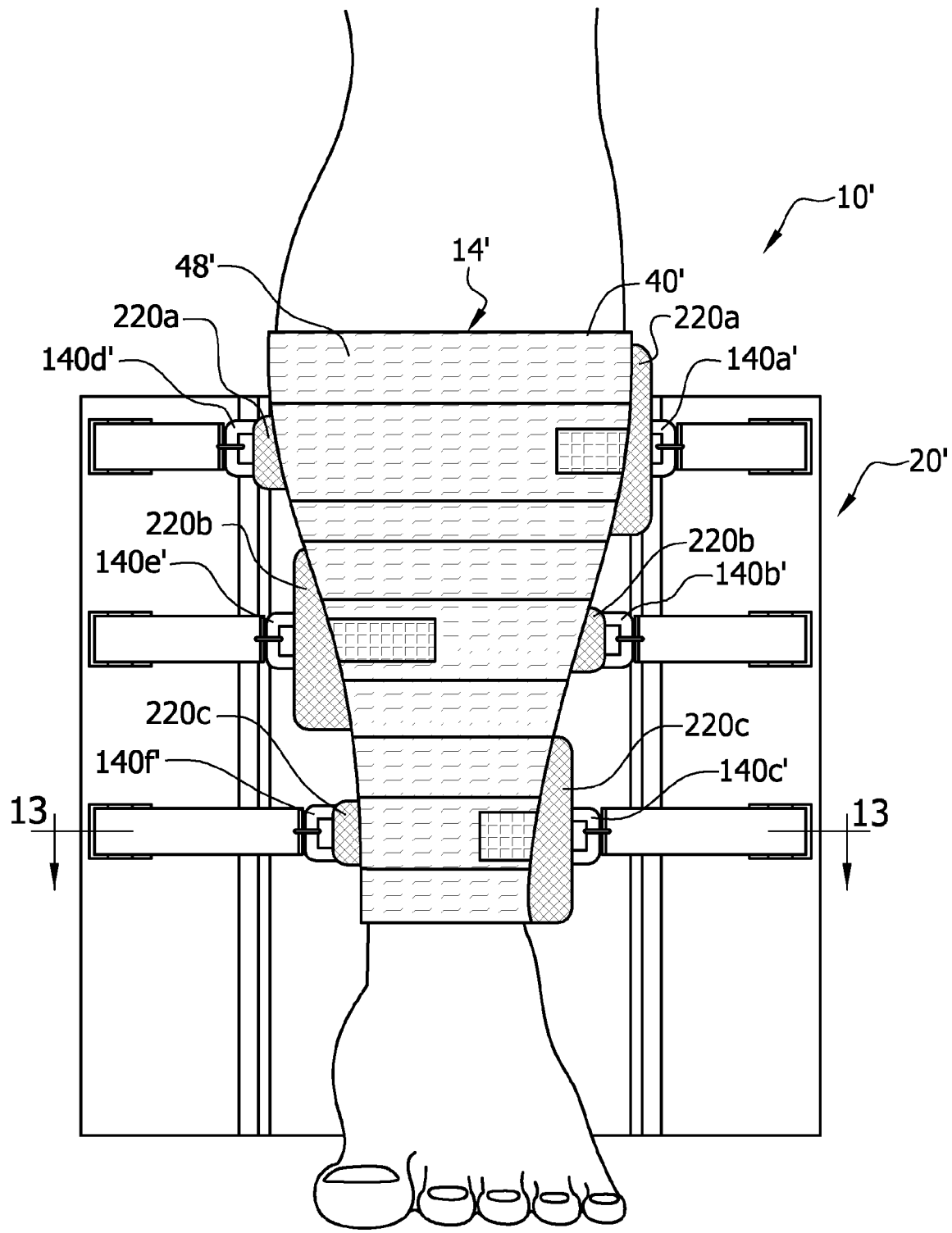
FIG. 12 is a front elevation of the garment of FIG. 11 placed on a leg and connected to the machine of FIG. 5.
Figure 13:
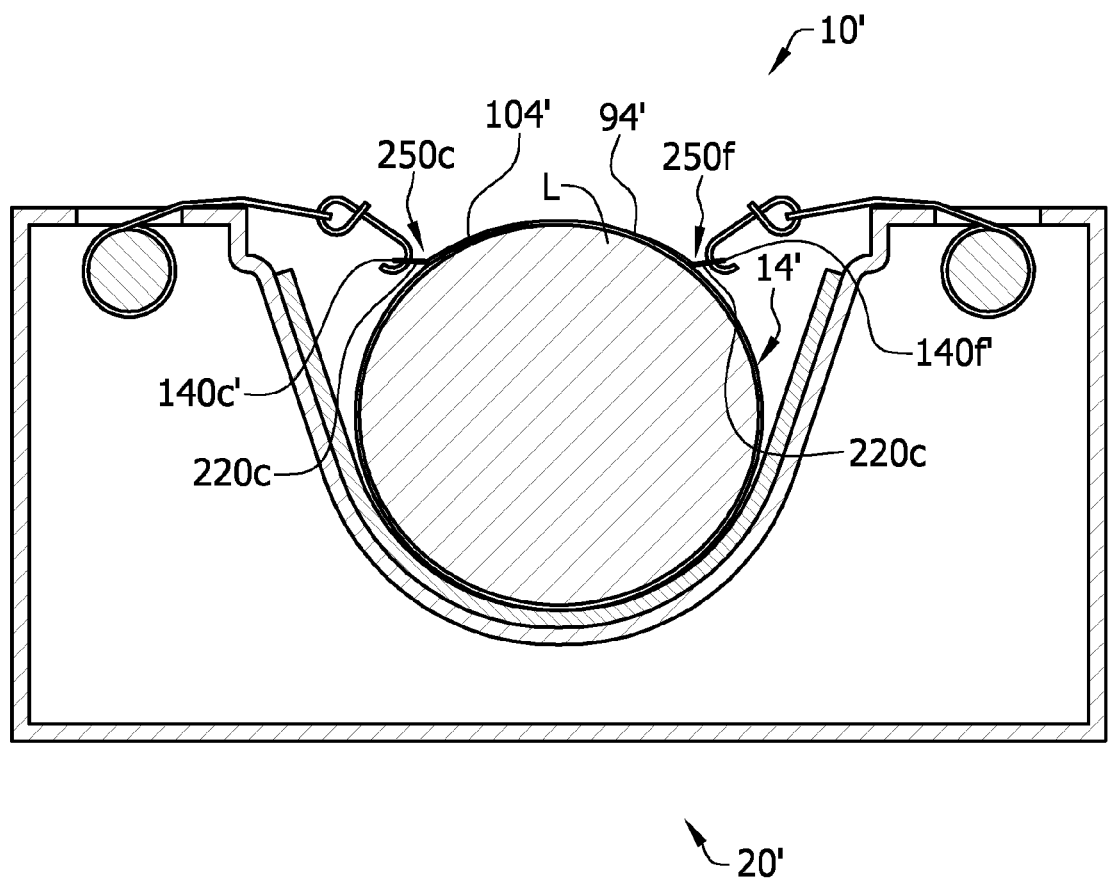
FIG. 13 is a section taken along the line 13-13 of FIG. 11.
Figure 14:
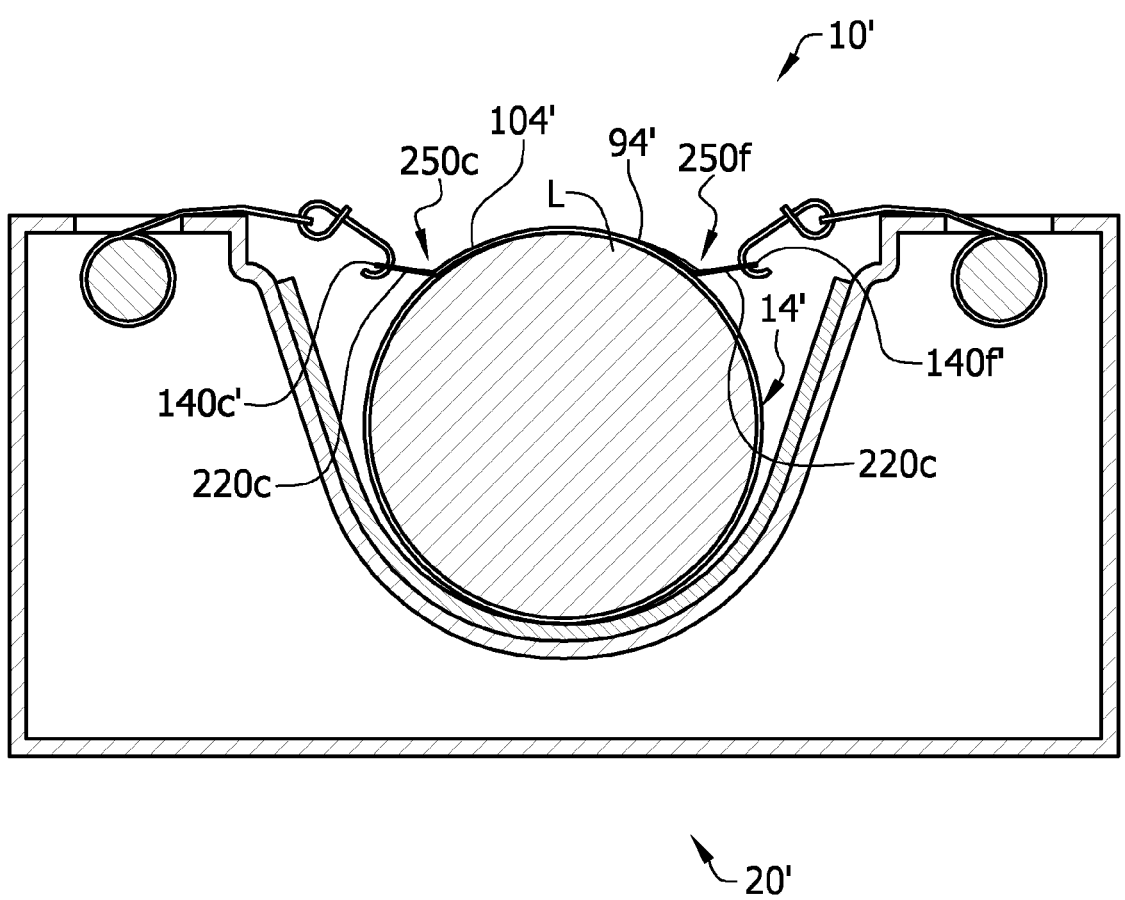
FIG. 14 is a view similar to FIG. 13 but showing the machine constricting the constriction members to apply compression to the leg.

As shown in FIG. 12, the connectors 140a'-140f' are mounted on the constriction members 220a-220c and are accessible so that the connectors may be connected to the machine 20' and the machine can transmit a force to the constriction members that constricts the sleeve 14'. The connectors 140a'-140f' on the constriction members 220a-220c are accessible through openings 250a-250f in the sleeve body 40' communicating with the cavity 230. In the illustrated embodiment, the openings 250a-250f are located at the free ends of the straps 90', 92', 94' and the free ends of the loops 100', 102', 104'.

The constriction members 220a-220c are independent of the sleeve body 40' in the sense that the constriction members are not affixed to the sleeve body and are relatively free to move within the sleeve body. The constriction members 220a-220c may be made of low friction material to facilitate movement within the sleeve body 40' and may be inelastic or elastic. Alternatively, portions of the constriction members 220a-220c may be affixed to the sleeve body 40' to limit the movement of the constriction members within the sleeve body. As shown in FIG. 11, the illustrated constriction members 220a-220c are limited in movement within the cavity 230 of the sleeve body 40' by engagement of edges 260a-260c of the constriction members with edges 270a-270c of the sleeve body defining the cavity at the loops 80', 82', 84' of the sleeve body. This limitation in movement prevents the constriction members 220a-220c from drifting to positions in which the connectors 140*a*'-140*f*' are no longer accessible through the openings 250*a*-250*f* at the free ends of the straps 90', 92', 94' and the free ends of the loops 100', 102', 104'. In other embodiments, the constriction members 220*a*-220*c* have no limitation in movement within the cavity 230 of the sleeve body 40'.

Desirably, the use of the constriction members 220*a*-220*c* makes it unnecessary to unfasten the fasteners 120*a*', 120*b*' on the sleeve 14' when the sleeve is connected to the machine 20'. As shown by comparison of FIG. 12 to FIG. 7, the hook fabric 120*a*' (FIG. 11) on the free ends of the straps 90', 92', 94' and the free ends of the loops 100', 102', 104' may remain fastened to the loop fabric 120*b*' (FIG. 11) on the sleeve 14' when the connectors 170*a*'-170*f*' on the machine 20' are connected to the connectors 140*a*'-140*f*' on the constriction members 220*a*-220*c*. This configuration enables the sleeve 14' to maintain a baseline compression on the limb L during active compression. The baseline compression is equivalent to the static compression applied to the limb L by the sleeve 14'.

The sleeve 14' is used much the same way as the sleeve 14. The sleeve 14' is placed on the limb L by placing the central portion 50' of the sleeve in longitudinal alignment with the limb, with the inner or patient contact surface 46' of the sleeve facing the limb. The side portions 54', 58' of the sleeve 14' are then folded over the limb L and secured using the fasteners 120*a*', 120*b*' such that the sleeve encircles the limb to apply static compression to the limb. For applying active compression, the machine 20' is connected to the connectors 140*a*'-140*f*' on the constriction members 220*a*-220*c*. As shown by comparison of FIGS. 13 and 14, the machine 20' transmits a force to the constriction members 220*a*-220*c* that constricts the sleeve 14'.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A hybrid compression garment adapted for use with a machine which is connectable to the compression garment and operable to create a force for constricting the compression garment for imparting active compression to a limb of a person, the compression garment comprising:

a sleeve adapted for placement on the limb for applying static compression to the limb; and a connecting device comprising multiple connectors on the sleeve configured for releasable connection of the sleeve to the machine, the connectors being operable to transmit, through said connectors, the force from the machine to the sleeve to constrict the sleeve without inflating the sleeve to apply active compression to said limb;

said connecting device being adapted for connection of the sleeve to said machine such that the sleeve can be used to apply said active compression to the limb and being adapted for disconnection of the sleeve from the machine such that the sleeve can be used to apply said static compression to the limb;

wherein the sleeve comprises a longitudinal central portion and side portions extending laterally outward from opposite sides of the central portion, said side portions comprising a plurality of sets of straps and loops, each set comprising a strap extending out from a first longitudinal side of the central portion and terminating in a free end and a loop extending out from a second opposite side of the central portion and terminating in a free end, the strap and loop of each set being generally in alignment with one another such that when the sleeve is placed on the limb with the central portion of the sleeve longitudinally aligned with the limb, the side portions of the sleeve may be folded over the limb and the free ends of the straps threaded through corresponding loops, the sleeve further comprising fasteners on the sleeve for holding the straps and loops in a position in which the sleeve encircles the limb to apply static compression to the limb.

2. A hybrid compression garment as set forth in claim 1 wherein the garment comprises multiple compression zones, at least one of the connectors being mounted on the sleeve within each compression zone.

3. A hybrid compression garment as set forth in claim 2 wherein the sleeve is adapted for placement on a leg of a person and the compression zones comprise an ankle compression zone, an intermediate compression zone, and a calf compression zone.

4. A hybrid compression garment as set forth in claim 3 wherein the connecting device comprises six connectors on the sleeve, two connectors in each compression zone, and wherein the connectors are at locations on the sleeve such that when the sleeve is placed on the leg the two connectors in each compression zone are positioned on or adjacent opposite sides of the leg.

5. A hybrid compression garment as set forth in claim 1 wherein the sleeve comprises a sleeve body having a patient contact surface and an outside surface, the sleeve further comprising a constriction member disposed within a cavity between the patient contact surface and the outside surface such that the constriction member is encapsulated at least partially within the sleeve body between the patient contact surface and the outside surface, at least some of said connectors being mounted on the constriction member, and said connectors being accessible through openings in the sleeve body communicating with the cavity such that the machine may be connected to the constriction member to transmit a force to the constriction member that constricts the sleeve.

6. A hybrid compression garment as set forth in claim 1 wherein the connectors on the sleeve are mounted adjacent the free ends of the straps and loops.

7. A hybrid compression garment as set forth in claim 1 in combination with the machine.

8. A hybrid compression system adapted for selectively applying static and active compression to a limb of a person, the compression system comprising:

a compression garment adapted for placement on the limb for applying static compression to the limb;

a machine which is connectable to the compression garment and operable to constrict the compression garment for imparting active compression to the limb, the machine including a frame which includes a bed for supporting the compression garment and the limb and an actuation system configured for releasable connection with the compression garment, the actuation system being configured for generating a force transmissible to the compression garment for constricting the compression garment;

the compression garment including a connecting device configured for releasable connection of the compression garment to the actuation system of the machine, the connecting device being operable to transmit, through said connecting device, the force from the actuation system of the machine to the compression garment to constrict the compression garment without inflating the compression garment to apply active compression to said limb; and said connecting device being adapted for connection of the compression garment to said machine such that the compression garment can be used to apply said active compression to the limb and being adapted for disconnection of the compression garment from the machine such that the compression garment can be used to apply said static compression to the limb;

wherein the connecting device comprises multiple connectors positioned and spaced along the length of the compression garment, and wherein the actuation system comprises corresponding multiple connectors spaced along opposite sides of the bed at intervals lengthwise of the bed generally corresponding to the spacing of the connectors along the compression garment, said connectors on the compression garment being configured for releasable connection to the connectors of the actuation system.

9. A hybrid compression system as set forth in claim 8 wherein the compression garment comprises a longitudinal central portion and side portions extending laterally outward from opposite sides of the central portion, said side portions being configured to overlap one another when the compression garment is placed on the limb, said connectors on the compression garment being located on said opposite side portions, and wherein said actuation system comprises one or more actuators on the frame for moving the connectors of the actuation system on at least one side of the bed such that when the connectors of the actuation system are connected to the connectors on the compression garment, forces in opposite directions are applied to respective overlapping side portions of the compression garment to constrict the compression garment.

10. A method of applying compression to a limb of a person, the method comprising:

placing a sleeve on the limb for applying static compression to the limb;

interfacing a connecting device on the sleeve with a machine that is independent of the sleeve;

constricting the sleeve without inflating the sleeve by transmitting a force generated by the machine to the sleeve through the connecting device for applying active compression to the limb;

wherein interfacing the connecting device on the sleeve with the machine comprises releasably connecting connectors on the machine to connectors on a constriction member encapsulated at least partially within the sleeve between a patient contact surface and an outside surface of the sleeve, and wherein constricting the sleeve comprises transmitting a force generated by the machine to the constriction member through said connectors on the constriction member.

11. A method as set forth in claim 10 further comprising discontinuing constriction of the sleeve, disconnecting the sleeve from the machine, and using the sleeve to apply said static compression to the limb.

12. A method as set forth in claim 10 wherein interfacing the connecting device with the machine comprises connecting connectors on the constriction member with an actuation system on the machine.

13. A method as set forth in claim 10 wherein constricting the sleeve comprises constricting the sleeve intermittently.

14. A method as set forth in claim 12 wherein constricting the sleeve further comprises constricting distal portions of the sleeve prior to constricting proximal portions of the sleeve to apply sequential compression to said limb.

15. A method as set forth in claim 13 wherein constricting the sleeve further comprises constricting distal portions of the sleeve more than proximal portions of the sleeve to apply gradient compression to said limb.

* * * * *